(12) United States Patent
Akahane et al.

(10) Patent No.: US 11,432,607 B2
(45) Date of Patent: Sep. 6, 2022

(54) ARTIFICIAL HAIR FIBER

(71) Applicant: DENKA COMPANY LIMITED, Tokyo (JP)

(72) Inventors: Takuya Akahane, Kamakura (JP); Masamichi Kanaoka, Kamakura (JP); Masashi Kume, Kamakura (JP)

(73) Assignee: DENKA COMPANY LIMITED, Tokyo (JP)

( * ) Notice: Subject to any disclaimer, the term of this patent is extended or adjusted under 35 U.S.C. 154(b) by 378 days.

(21) Appl. No.: 16/614,189

(22) PCT Filed: May 23, 2018

(86) PCT No.: PCT/JP2018/019835
§ 371 (c)(1),
(2) Date: Nov. 15, 2019

(87) PCT Pub. No.: WO2018/221348
PCT Pub. Date: Dec. 6, 2018

(65) Prior Publication Data
US 2020/0077725 A1 Mar. 12, 2020

(30) Foreign Application Priority Data
May 30, 2017 (JP) .............................. JP2017-106106

(51) Int. Cl.
*A41G 3/00* (2006.01)
*C08L 27/06* (2006.01)
*D01F 6/48* (2006.01)

(52) U.S. Cl.
CPC ............ *A41G 3/0083* (2013.01); *C08L 27/06* (2013.01); *D01F 6/48* (2013.01); *C08L 2203/12* (2013.01);
(Continued)

(58) Field of Classification Search
CPC .................................................... A41G 3/0083
See application file for complete search history.

(56) References Cited

U.S. PATENT DOCUMENTS 4,311,761 A * 1/1982 Kanbara ................ D01D 5/253
132/53
4,600,743 A * 7/1986 Shizuki ..................... D01F 1/09
524/377
(Continued)

FOREIGN PATENT DOCUMENTS

JP S60-014729 Y2 5/1985
JP H08-296115 A 11/1996
(Continued)

OTHER PUBLICATIONS

Jul. 31, 2018 International Search Report issued in International Patent Application No. PCT/JP2018/019835.

*Primary Examiner* — Irina Krylova
(74) *Attorney, Agent, or Firm* — Oliff PLC (57) ABSTRACT

A polyvinyl chloride-based fiber for artificial hair that has excellent low glossiness and grip performance when woven and can be stably spun. Configuring a fiber for artificial hair using a polyvinyl chloride-based resin composition, wherein the polyvinyl chloride-based resin includes, at predetermined blending amounts, a polyvinyl chloride-based resin (A) having a viscosity-average polymerization degree of 450-1,700 and a crosslinked vinyl chloride-based resin (B) in which the viscosity-average polymerization degree of a component that dissolves in tetrahydrofuran is 1,800-2,300, the difference between the viscosity-average polymerization degree of the polyvinyl chloride-based resin (A) and the viscosity-average polymerization degree of the THF-soluble component of the crosslinked vinyl chloride-based resin (B) is in a predetermined range, and the cross-sectional shape of the fiber for artificial hair has a first projection, a second
(Continued)

projection, and a third projection and the lengths and widths thereof satisfy predetermined conditions.

4 Claims, 1 Drawing Sheet

(52) U.S. Cl.
CPC .... *C08L 2205/025* (2013.01); *D10B 2503/08* (2013.01)

(56) References Cited

U.S. PATENT DOCUMENTS

| | | | | |
|---|---|---|---|---|
| 2003/0157319 A1* | 8/2003 | Boyle | ................... | D01D 5/253 |
| | | | | 428/364 |
| 2008/0139705 A1* | 6/2008 | Adachi | .................... | D01F 6/48 |
| | | | | 524/80 |
| 2008/0210250 A1* | 9/2008 | Horihata | ................... | D01F 6/32 |
| | | | | 132/54 |
| 2018/0051393 A1* | 2/2018 | Meinders | ................. | D01D 5/24 |

FOREIGN PATENT DOCUMENTS

| | | | |
|---|---|---|---|
| JP | H11-061555 A | 3/1999 | |
| JP | 2000-191871 A | 7/2000 | |
| JP | 2010-024586 A | 2/2010 | |
| JP | 2011-149134 A | 8/2011 | |
| WO | 2006/093009 A1 | 9/2006 | |
| WO | 2006/135059 A1 | 12/2006 | |
| WO | 2008/029727 A1 | 3/2008 | |
| WO | 2017/221773 A1 | 12/2017 | |

* cited by examiner

ARTIFICIAL HAIR FIBER

TECHNICAL FIELD

The present invention pertains to a fiber for artificial hair that uses a polyvinyl chloride-based resin composition.

BACKGROUND ART

Polyvinyl chloride-based fibers have excellent strength, ductility, etc. and are often used as fibers for artificial hair that constitute hair decorations. However, there are as yet no satisfactory designs for fibers for artificial hair comprising polyvinyl chloride-based fibers in relation to low glossiness, grip when woven, and spinnability, and trial and error is ongoing.

In Patent Document 1, concavities were added to each side of the cross-section to lower glossiness, but this alone is insufficient. In Patent Document 2, a crosslinked vinyl chloride-based resin was added to a vinyl chloride-based resin in order to impart low glossiness and a methacrylic acid alkyl ester was added in order to improve spinnability, but the low glossiness in this combination is insufficient. In Patent Document 3, the invention comprises a resin composition of a vinyl chloride-based resin and a crosslinked vinyl chloride-based resin having a specified viscosity-average molecular weight and the cross-sectional shape presents shapes comprising circles, parabolas, and ellipses, but low glossiness is insufficient and there is the problem of thread slipping when woven and weaving being difficult.

In Patent Document 4, bulk height and ease of weaving are imparted in a Y-shape having projections in three directions, but in the shape and material design of the Y-shape, the linear parts of the Y reflect light and therefore low glossiness is insufficient. Further, in this Y-shape, the contact area between yarns decreases and frictional resistance decreases, so the yarn readily slips.

[Patent Document 1] JP S60-14729 U
[Patent Document 2] JP 2000-191871 A
[Patent Document 3] WO 2006/093009 A
[Patent Document 4] WO 2008/029727 A

SUMMARY OF INVENTION

Technical Problem

The present invention addresses the problem of providing a polyvinyl chloride-based fiber for artificial hair that has excellent low glossiness, has grip performance when woven, and can be stably spun.

Solution to Problem

As a result of intensive research, the present inventors discovered that, when using a specific polyvinyl chloride-based resin composition and the cross-sectional shape has projections in three directions and the lengths and widths of the projections satisfy predetermined conditions, a polyvinyl chloride-based fiber for artificial hair having superior low glossiness, grip when woven, and spinnability is obtained. That is, the present invention employs the following means to solve the problem.

[1] A fiber for artificial hair containing a polyvinyl chloride-based resin composition, wherein
the polyvinyl chloride-based resin composition comprises 90-99 parts by mass of a polyvinyl chloride-based resin (A) having a viscosity-average polymerization degree of 450-1,700 and 1-10 parts by mass of a crosslinked vinyl chloride-based resin (B) having a viscosity-average polymerization degree for a component that is soluble in tetrahydrofuran of 1,800-2,300,
the difference between the viscosity-average polymerization degree of the polyvinyl chloride-based resin (A) and the viscosity-average polymerization degree for the component that is soluble in tetrahydrofuran of the crosslinked vinyl chloride-based resin (B) is 600-1,850, and,
the cross-sectional shape of the fiber for artificial hair has a first projection, a second projection, and a third projection extending outward from a center C of the cross-sectional shape and when the length of the first projection from the center C is set as $L_1$, the length of the second projection from the center C is set as $L_2$, and the length of the third projection from the center C is set as $L_3$, the shapes of the projections satisfy (2) and (3) below.
(2) The ratio of a width $W_{1(0.15)}$ of the first projection at a distance of $0.15L_1$ from the center C and a width $W_{1(0.9)}$ of the first projection at a distance of $0.9L_1$ from the center C ($W_{1(0.15)}/W_{1(0.9)}$) is 1.2-2.5.
(3) at least one of the ratio of a width $W_{2(0.15)}$ of the second projection at a distance of $0.15L_2$ from the center C and a width $W_{2(0.9)}$ of the first projection at a distance of $0.9L_2$ from the center C ($W_{2(0.15)}/W_{2(0.9)}$) and the ratio of a width $W_{3(0.15)}$ of the third projection at a distance of $0.15L_3$ from the center C and a width $W_{3(0.9)}$ of the third projection at a distance of $0.9L_3$ from the center C ($W_{3(0.15)}/W_{3(0.9)}$) is 1.8-2.5.
[2] The fiber for artificial hair described in [1], further satisfying (1) below.
(1) the length $L_1$ of the first projection, the length $L_2$ of the second projection, and the length $L_3$ of the third projection from the center C satisfy $L_3 \leq L_2$, $0.8L_1 \leq L_2 \leq 0.95L_1$, and $0.8L_1 \leq L_3 \leq 0.95L_1$.
[3] The fiber for artificial hair described in [1] or [2], containing 0.01-1.0 parts by mass of an antistatic agent with respect to a total of 100 parts by mass of the polyvinyl chloride-based resin (A) and the crosslinked vinyl chloride-based resin (B).
[4] The fiber for artificial hair described in any one of [1] to [3], containing 0.1-5.0 parts by mass of at least one thermal stabilizer selected from tin-based thermal stabilizers, Ca—Zn-based thermal stabilizers, hydrotalcite-based thermal stabilizers, epoxy-based thermal stabilizers, and β-diketone-based thermal stabilizers with respect to a total of 100 parts by mass of the polyvinyl chloride-based resin (A) and the crosslinked vinyl chloride-based resin (B).

Advantageous Effects of Invention

According to the present invention, a polyvinyl chloride-based fiber for artificial hair that has excellent low glossiness, has grip performance when woven, and can be stably spun can be provided.

DESCRIPTION OF EMBODIMENTS

One embodiment of the present invention shall be explained in detail below. The present invention is not limited to the following embodiment and can be carried out with the addition of appropriate modifications so long as the effects of the present invention are not hindered.

[Fiber for Artificial Hair]

The fiber for artificial hair is a fiber formed by using a polyvinyl chloride-based resin composition containing a polyvinyl chloride-based resin (A) and a crosslinked vinyl chloride resin (B) (hereafter, simply referred to as "resin composition").

(Polyvinyl Chloride-Based Resin (A))

The polyvinyl chloride-based resin (A) is not particularly limited and a homopolymer resin that is a homopolymerized product of a conventionally-known vinyl chloride or various conventionally-known copolymer resins can be used. Copolymer resins of vinyl chloride and vinyl esters such as vinyl chloride-vinyl acetate copolymer resins and vinyl chloride-vinyl propionate copolymer resins; copolymer resins of vinyl chloride and acrylic acid esters such as vinyl chloride-butyl acrylate copolymer resins and vinyl chloride-2-ethylhexyl acrylate copolymer resins; copolymer resins of vinyl chloride and olefins such as vinyl chloride-ethylene copolymer resins and vinyl chloride-propylene copolymer resins; vinyl-chloride-acrylonitrile copolymer resins, etc. are representative examples of the copolymer resin. Preferred examples of the polyvinyl chloride-based resin (A) include homopolymer resins that are homopolymerized products of vinyl chloride, vinyl chloride-ethylene copolymer resins, vinyl chloride-vinyl acetate copolymer resins, etc. The content of comonomers in the copolymer resin is not particularly limited and can be determined in accordance with the molding workability into a fiber, the properties of the fiber, etc.

The viscosity-average polymerization degree of the polyvinyl chloride-based resin (A) is in the range 450-1,700 in order to obtain sufficient strength and thermal resistance as a fiber. If the viscosity-average polymerization degree of the polyvinyl chloride-based resin (A) is less than 450, there is little interlocking of the resin and the strength falls. Further, if the viscosity-average polymerization degree exceeds 1,700, gelling does not occur, the fiber becomes readily cut, and productivity decreases. When a homopolymer resin of polyvinyl chloride is used, it is preferable in terms of satisfying molding workability and fiber properties that the viscosity-average polymerization degree is in the area of 650-1,450. When a copolymer is used, it depends on the content of the comonomers, but the viscosity-average polymerization degree is preferably in the area of 1,000-1,700. 200 mg of the resin is dissolved in 50 mL of nitrobenzene, the polymer solution is placed in a 30° C. thermostatic oven, the specific viscosity is measured using an Ubbelohde-type viscometer and the viscosity-average polymerization degree is calculated according to JIS-K6721.

The content of the polyvinyl chloride-based resin (A) is 90-99 parts by mass and preferably 95-97 parts by mass with respect to a total of 100 parts by mass of the polyvinyl chloride-based resin (A) and the crosslinked vinyl chloride-based resin (B) discussed below. If the content exceeds 99 parts by mass, the low glossiness and weavability of the obtained fiber fall and if the content is less than 90 parts by mass, spinnability falls.

Further, in terms of spinnability, the content of the polyvinyl chloride-based resin (A) in the entire resin composition is preferably no less than 50% by mass and more preferably no less than 80% by mass.

The polyvinyl chloride-based resin (A) can be manufactured by emulsion polymerization, bulk polymerization, suspension polymerization, etc. In consideration of initial colorability, etc. of the fiber, a polymer manufactured with suspension polymerization is preferred.

(Crosslinked Vinyl Chloride-Based Resin (B))

The crosslinked vinyl chloride-based resin (B) is easily obtained by, when suspension polymerizing, microsuspension polymerizing, or emulsion polymerizing vinyl chloride in an aqueous medium, adding a multifunctional monomer and polymerizing. At this time, a diacrylate compound such as polyethylene glycol diacrylate or bisphenol A-modified diacrylate is particularly preferred as the multifunctional monomer to be used. The crosslinked vinyl chloride-based resin (B) has a crosslinked structure and is a mixture of a gel component having a vinyl chloride insoluble in tetrahydrofuran as a main component and a polyvinyl chloride component that is soluble in tetrahydrofuran.

The viscosity-average polymerization degree of the component that dissolves in tetrahydrofuran in the crosslinked vinyl chloride-based resin (B) is, in consideration of weavability and spinnability of the yarn, 1,800-2,300 and more preferably 1,900-2,200. If the viscosity-average polymerization degree of the component that dissolves in tetrahydrofuran is less than 1,800, the weavability is not sufficient. Conversely, if the viscosity-average polymerization degree exceeds 2,300, the yarn readily breaks during spinning.

The viscosity-average polymerization degree of the component that dissolves in tetrahydrofuran in the crosslinked vinyl chloride-based resin (B) is measured as follows. 1 g of the crosslinked vinyl chloride-based resin (B) is added to 60 mL of tetrahydrofuran and let alone for 24 hours. Then the resin is sufficiently dissolved by using an ultrasonic cleaning machine. The insoluble component in the tetrahydrofuran solution is separated by using an ultracentrifugal separator (30,000 rpm×1 hour) and the supernatent THF solvent is extracted. Then the THF solvent is volatilized and the viscosity-average polymerization degree is measured with a method similar to that for the polyvinyl chloride-based resin (A).

The difference between the viscosity-average polymerization degree of the polyvinyl chloride-based resin (A) and the viscosity-average polymerization degree for the component that dissolves in tetrahydrofuran-in the crosslinked vinyl chloride-based resin (B) is 600-1,850, and more preferably, 800-1,500 in order to obtain sufficient low glossiness. If the difference is less than 600, the low glossiness is insufficient and conversely, if the difference exceeds 1,500, the yarn readily breaks during spinning.

The content of the crosslinked vinyl chloride-based resin (B) is 1-10 parts by mass with respect to the 90-99 parts by mass of the polyvinyl chloride-based resin (A) and preferably 3-5 parts by mass of the crosslinked vinyl chloride-based resin (B) are added to 95-97 parts by mass of the polyvinyl chloride-based resin (A). If there is less than 1 part by mass of the crosslinked vinyl chloride-based resin (B), the low glossiness and weavability of the obtained fiber fall and if the crosslinked vinyl chloride-based resin (B) exceeds 10 parts by mass, spinnability falls, which is not preferable.

<Additives>

The resin composition can contain an antistatic agent, a thermal stabilizer, and a lubricant, as necessary.

(Antistatic Agent)

A non-ionic, cationic, anionic, or amphoteric substance can be used as the antistatic agent and the content thereof is preferably 0.01-1 parts by mass with respect to the total of 100 parts by mass of the polyvinyl chloride-based resin (A) and the crosslinked vinyl chloride-based resin (B). By setting the content to no less than 0.01 parts by mass, the generation of static electricity can be prevented. As a result thereof, the problem of bundling yarns becoming more difficult, yarn readily entangling in a winding process, and the yarn breaking, which readily occurs due to the generation of static electricity, can be prevented. Further, by setting the content of the antistatic agent to no greater than 1 part by mass, the invention can be made economically advantageous.

(Thermal Stabilizer)

Conventionally known substances can be used as the thermal stabilizer. Among these, using at least one selected from Ca—Zn-based thermal stabilizers, hydrotalcite-based stabilizers, tin-based thermal stabilizers, zeolite-based thermal stabilizers, epoxy-based thermal stabilizers, and β-diketone-based thermal stabilizers is desirable. The thermal stabilizer is used to improve thermal decomposition during molding, long-run properties, and improve the color tone of filaments and combined use of a Ca—Zn-based thermal stabilizer and a hydrotalcite-based thermal stabilizer is preferred, which particularly preferably, has an excellent balance between mold workability and spinning properties.

There are Ca—Zn-based thermal stabilizers such as zinc stearate, calcium stearate, zinc 12-hydroxystearate, and calcium 12-hydroxystearate. As hydrotalcite-based thermal stabilizers, there is, for example, Alcamizer manufactured by Kyowa Chemical Industry Co., Ltd., etc. As tin-based stabilizers, there are mercapto tin-based thermal stabilizers such as dimethyl tin mercapto, dimethyl tin mercaptide, dibutyl tin mercapto, dioctyl tin mercapto, dibutyl tin mercapto polymers, and dioctyl tin mercapto acetate; tin maleate-based thermal stabilizers such as dimethyl tin maleate, dibutyl tin stearate, dioctyl tin maleate, and dioctyl tin maleate polymers; and tin laurate-based thermal stabilizers such as dimethyl tin laurate, dibutyl tin laurate, and dioctyl tin laurate. As epoxy-based stabilizers, there are, for example, epoxidized soy oil, epoxidized linseed oil, etc. As β diketone-based thermal stabilizers, there are, for example, stearoylbenzoyl methane (SBM), dibenzoyl methane (DBM), etc.

As hydrotalcite-based thermal stabilizers, specifically, there are hydrotalcite compounds, for example, complex chlorides comprising magnesium and/or alkali metals and aluminum or zinc, complex chlorides comprising magnesium and aluminum, etc. Furthermore, the stabilizer may be a substance from which crystallization water has been dehydrated. Moreover, the hydrotalcite compounds may be natural or synthetic products and the synthesis method for synthetic products may be conventionally known methods.

The content of the thermal stabilizer is preferably 0.1-5.0 parts by mass with respect to a total 100 parts by mass of the polyvinyl chloride-based resin (A) and the crosslinked vinyl chloride-based resin (B). By setting the content to no less than 0.1 parts by mass, yellowing due to thermal degradation of the resin composition can be prevented. Further, by setting the content to no greater than 5.0 parts by mass, the invention can be made economically advantageous.

(Lubricant)

Conventionally known substances can be used as the lubricant, but it is particularly preferable that the lubricant is at least one selected from the group consisting of metal soap-based lubricants, polyethylene-based lubricants, higher fatty acid-based lubricants, ester-based lubricants, and higher alcohol-based lubricants. The lubricant can reduce friction between a metal surface of a processing machine and a resin or friction between resins, improve flowability, and improve workability.

Examples of metal soap-based lubricants include, for example, metal soaps such as stearates, laurates, palmitates, and oleates of Na, Mg, Al, Ca, Ba, etc. Examples of higher fatty acid-based lubricants include, for example, saturated fatty acids such as stearic acid, myristic acid, palmitic acid, lauric acid, and capric acid, unsaturated fatty acids such as oleic acid, mixtures thereof, etc. Examples of higher alcohol-based lubricants include stearyl alcohol, palmityl alcohol, myristyl alcohol, lauryl alcohol, oleyl alcohol, etc. Examples of ester-based lubricants include ester-based lubricants comprising alcohol and a fatty acid; pentaerythritol-based lubricants such as monoesters, diesters, triesters, and tetraesters of pentaerythritol or dipentaerythritol and a higher fatty acid or mixtures thereof; and ester montanoic acid wax-based lubricants of montanoic acid and a higher alcohol such as stearyl alcohol, palmityl alcohol, myristyl alcohol, lauryl alcohol, and oleyl alcohol.

The content of the lubricant is preferably 0.2-5.0 parts by mass with respect to the total 100 parts by mass of the polyvinyl chloride-based resin (A) and the crosslinked vinyl chloride-based resin (B). By setting the content to no less than 0.2 parts by mass, flowability becoming poorer and workability worsening can be suppressed. Further, by setting the content to no greater than 5.0 parts by mass, the friction between a metal surface of a processing machine and a resin becoming small can be prevented and the resin can be stably extruded.

In the present embodiment, in accordance with the objective, other publicly known blending agents to be used in the polyvinyl chloride-based resin composition can be added in ranges in which they do not hinder the effects of the present invention. As examples of a blending agent, there are processing aids, plasticizers, reinforcement agents, ultraviolet absorbing agents, antioxidants, fillers, flame retardants, pigments, initial coloring improvement agents, conductivity-imparting agents, fragrances, etc.

(Cross-Sectional Shape of the Fiber for Artificial Hair)

Figure 1:
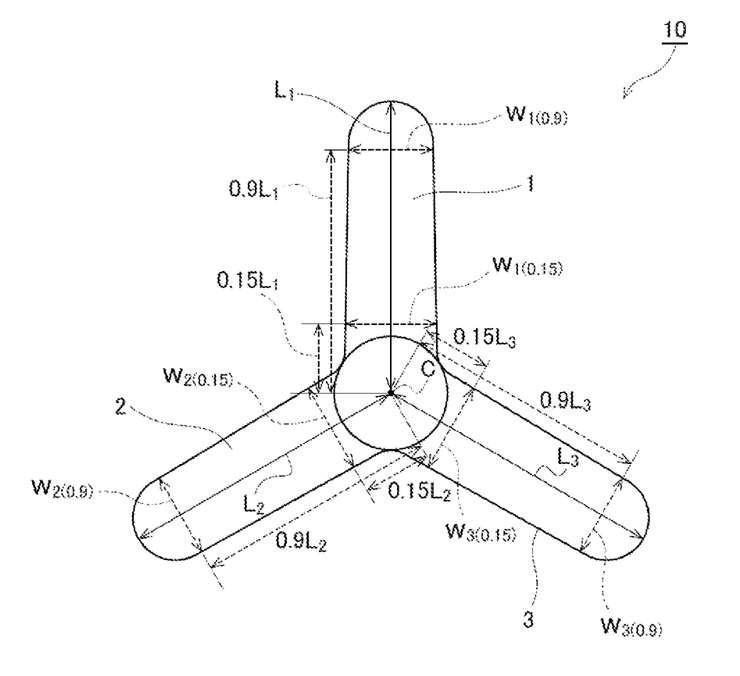
FIG. 1 A FIGURE showing the cross-sectional shape of the fiber for artificial hair according to one embodiment of the present invention.

The fiber for artificial hair preferably has an almost uniform cross-sectional shape in the lengthwise direction. FIG. 1 is a cross-sectional drawing orthogonal to the lengthwise direction of the fiber for artificial hair 10. As shown in FIG. 1, the cross-sectional shape of the fiber for artificial hair 10 has a first projection, a second projection, and a third projection extending outward from the center C of the cross-sectional shape (hereafter referred to simply as "projection 1", "projection 2", and "projection 3"). Projections 1-3 are disposed spaced from one another and thereby the cross-sectional shape of the fiber for artificial hair 10 becomes a Y-shape. Projections 1-3 may be disposed with equiangular spacing. The center C means the center of the largest inscribed circle in the center of the cross-sectional shape of the fiber for artificial hair 10.

When the length of the first projection from the center C is set as $L_1$, the length of the second projection from the center C is set as $L_2$, and the length of the third projection from the center C is set as $L_3$, the shapes of the first projection, the second projection, and the third projection satisfy (2) and (3) below.

(2) the ratio of a width $W_{1(0.15)}$ of the first projection at a distance of $0.15L_1$ from the center C and a width $W_{1(0.9)}$ of the first projection at a distance of $0.9L_1$ from the center C ($W_{1(0.15)}/W_{1(0.9)}$) is 1.2-2.5.

(3) at least one of the ratio of a width $W_{2(0.15)}$ of the second projection at a distance of $0.15L_2$ from the center C and a width $W_{2(0.9)}$ of the second projection at a distance of $0.9L_2$ from the center C ($W_{2(0.15)}/W_{2(0.9)}$) and the ratio of a width $W_{3(0.15)}$ of the third projection at a distance of $0.15L_3$ from the center C and a width $W_{3(0.9)}$ of the third projection at a distance of $0.9L_3$ from the center C ($W_{3(0.15)}/W_{3(0.9)}$) is 1.8-2.5.

If the ratio of width $W_{1(0.15)}$ and width $W_{1(0.9)}$ of the first projection ($W_{1(0.15)}/W_{1(0.9)}$) is less than 1.2, gaps readily form when the fiber is bundled into a yarn and there is little contact between yarns, so frictional force decreases and grip worsens. Conversely, if the ratio exceeds 2.5, spinnability worsens. $W_{1(0.15)}/W_{1(0.9)}$ is more preferably in the range of 1.5-2.3.

If either of the ratio of width $W_{2(0.15)}$ and width $W_{2(0.9)}$ of the second projection ($W_{2(0.15)}/W_{2(0.9)}$) and the ratio of width $W_{3(0.15)}$ and width $W_{3(0.9)}$ of the third projection ($W_{3(0.15)}/W_{3(0.9)}$) is less than 1.8, gaps readily form when the fiber is bundled into a yarn and there is little contact between yarns, so frictional force decreases and grip worsens. Conversely, if either ratio exceeds 2.5, spinnability worsens. $W_{2(0.15)}/W_{2(0.9)}$ and/or $W_{3(0.15)}/W_{3(0.9)}$ is more preferably in the range 1.7-2.1.

Length $L_1$ of the first projection, length $L_2$ of the second projection, and length $L_3$ of the third projection may all be the same or may be different, but preferably further satisfy (1) below. From the point of spinnability, length $L_1$ of the first projection, length $L_2$ of the second projection, and length $L_3$ of the third projection are preferably 50-90 μm.

The measurement method for lengths $L_1$, $L_2$, and $L_3$ of the first projection, the second projection, and the third projection is to set the center of the largest inscribed circle in the center of the Y-shaped cross-section as the center C, take ten measurements of the positions of the apexes (projection end) of the projections in the three directions from the center, and take the mean value thereof. The widths $W_{1(0.15)}$, $W_{2(0.15)}$, and $W_{3(0.15)}$ are the widths of projections 1-3 at points $0.15L_1$, $0.15L_2$, and $0.15L_3$ in the direction toward the respective apexes from the center C. Further, widths $W_{1(0.9)}$, $W_{2(0.9)}$, and $W_{3(0.9)}$ are the widths of projections 1-3 at points $0.9L_1$, $0.9L_2$, and $0.9L_3$ in the direction toward the respective apexes from the center C. The measurements of the lengths and widths, can be measured by using, for example, a VHX-5000 digital microscope manufactured by Keyence Corporation, etc.

The shapes of the first projection, the second projection, and the third projection preferably satisfy (1)-(3) below.
(1) The lengths $L_1$, $L_2$, and $L_3$ from the center C satisfy $L_3 \leq L_2$, $0.8L_1 \leq L_2 \leq 0.95L_1$, and $0.8L_1 \leq L_3 \leq 0.95L_1$.
(2) the ratio of the width $W_{1(0.15)}$ of the first projection at a distance of $0.15L_1$ from the center C and the width $W_{1(0.9)}$ of the first projection at a distance of $0.9L_1$ from the center C ($W_{1(0.15)}/W_{1(0.9)}$) is 1.2-2.5.
(3) at least one of the ratio of the width $W_{2(0.15)}$ of the second projection at a distance of $0.15L_2$ from the center C and the width $W_{2(0.9)}$ of the second projection at a distance of $0.9L_2$ from the center C ($W_{2(0.15)}/W_{2(0.9)}$) and the ratio of the width $W_{3(0.15)}$ of the third projection at a distance of $0.15L_3$ from the center C and the width $W_{3(0.9)}$ of the third projection at a distance of $0.9L_3$ from the center C ($W_{3(0.15)}/W_{3(0.9)}$) is 1.8-2.5.

By the lengths $L_1$, $L_2$, and $L_3$ from the center C satisfying all the relationships $L_3 \leq L_2$, $0.8L_1 \leq L_2 \leq 0.95L_1$, and $0.8L_1 \leq L_3 \leq 0.95L_1$, grip can be further increased and more stable melt spinning can be performed. From the point of spinnability, length $L_1$ of the first projection is preferably 50-90

[Manufacturing Method for the Fiber for Artificial Hair]

The fiber for artificial hair is preferably manufactured by mixing all the raw materials, making a primary pellet compound, and then using publicly known melt spinning.

(Mixture and Production of Pellets)

The antistatic agent, the thermal stabilizer, the lubricant, and other blending agents are appropriately mixed with the polyvinyl chloride-based resin (A) and the crosslinked vinyl chloride-based resin (B) at predetermined ratios and, after stirring and mixing with a conventionally known mixer, the mixture is made into a pellet compound (pellet-like resin composition) with an extruder. For example, a pellet compound is obtained by melt mixing a powder compound (powder-like resin composition) obtained by using a Henschel mixer, a super mixer, a ribbon blender, etc. as the conventionally known mixer.

The manufacturing method for the powder compound may be a hot blend or a cold blend and normal conditions can be used as the manufacturing conditions. Preferably, in order to reduce the volatile components in the composition, using a hot blend in which the cut temperature when blending is raised to 105-155° C. is favorable.

The manufacture of the pellet compound can be made a method similar to manufacturing methods for normal vinyl chloride-based pellet compounds. For example, the pellet compound can be made by using a single screw extruder, a different-direction twin-screw extruder, a conical twin-screw extruder, a same-direction twin-screw extruder, a co-kneader, a planetary gear extruder, or a kneader such as a roll kneader. The conditions when manufacturing the pellet compound are not particularly limited, but it is preferable that the resin temperature be set so as to be no greater than 185° C. in order to prevent thermal degradation of the polyvinyl chloride-based resin composition. Further, in order to remove pieces of metal originating from the screw or fibers stuck to protective gloves, of which small quantities may contaminate the pellet compound, a mesh can be installed near the tip of the screw. A cold cut method can be employed in manufacturing the pellets. It is possible to employ means to remove chips (fine powder generated when manufacturing the pellets), etc. that can contaminate the pellet compound when cold cutting. Further, when used for a long period of time, nicks arise in cutter blades and chips become more readily generated, so it is preferable that blades are appropriately replaced.

(Spinning)

Pellets obtained as above are extruded as a resin under conditions for good spinnability using a nozzle that has projections in three directions with a cylinder temperature of 150-190° C. and a nozzle temperature in the range 180±15° C. and melt spun. The cross-sectional shape of the nozzle is set such that the cross-sectional shape of the obtained fiber for artificial hair satisfies the conditions discussed below.

The unstretched melt-spun yarn (polyvinyl chloride-based resin composition fibers) from the nozzle is introduced to a heating cylinder (heating cylinder temperature: 250° C.) and momentarily heat treated and wound by a winder installed at a position roughly 4.5 m directly below the nozzle. The strands are as-is unstretched yarn. During this winding, the winding rate is adjusted such that the fineness of the unstretched yarn is 175-185 deniers.

When the polyvinyl chloride-based resin composition is made into an unstretched yarn, a conventionally known extruder can be used. For example, a single screw extruder, a different-direction twin-screw extruder, a conical twin-screw extruder, etc. can be used, but it is particularly preferable that a single screw extruder wherein the bore has a diameter of about 35-85 mm or a conical extruder wherein the bore is about 35-50 mm ø is used. If the bore is too large, there are cases of the extrusion amount becoming large, the nozzle pressure becoming too great, and the resin temperature rising and degradation readily occurring.

(Stretching and Heat Treatment)

Next, the fiber for artificial hair is manufactured by, after the unstretched yarn is stretched to three times its length with a stretcher (105° C. in air atmosphere), performing heat treatment at 0.75 times using a heat treatment machine (110° C. in air atmosphere) (heat shrinking until the total fiber length shrinks to a length 75% of that before treatment) and configuring such that the fineness is 58-62 deniers.

(Gear Working)

The fiber for artificial hair may be gear worked, as necessary. Gear working is a method for crimping by passing a fiber bundle between two meshing high-temperature gears and the materials of the gears to be used, the gear corrugation shape, the number of teeth of the gears, etc. are not particularly limited. The crimp corrugation can change due to the fiber material, fineness, the pressure conditions between the gears, etc., but in the present embodiment, the crimp corrugation can be controlled by the depth of the grooves in the gear corrugation, the surface temperatures of the gears, and the working speed. These working conditions are not particularly limited, but the depth of the grooves in the gear corrugation is preferably 0.2-6 mm and more preferably 0.5-5 mm, the gear surface temperature is preferably 30-100° C. and more preferably 40-80° C., and the working speed is preferably 0.5-10 m/min and more preferably 1.0-8.0 m/min.

The total fineness of the fiber bundle when gear working is not particularly limited, but is 100,000-2,000,000 decitex and more preferably 500,000-1,500,000 decitex. If the total fineness of the fiber bundle is less than 100,000 decitex, productivity of the gear working worsens and furthermore, there are cases of yarn breakage when gear crimping. Meanwhile, if the total fineness of the fiber bundle exceeds 2,000,000 decitex, there are cases in which a uniform corrugation is not readily obtained, (Fiber for Artificial Hair)

The polyvinyl chloride-based fiber for artificial hair of the present embodiment obtained as above can be manufactured with the characteristics of low glossiness and high gripping performance when woven and also with favorable spinnability. The reason that low glossiness was able to be imparted even with a Y-shaped cross section is because the blending amount of the crosslinked vinyl chloride-based resin (B) was made suitable and the difference between the viscosity-average polymerization degree of the polyvinyl chloride-based resin (A) and the viscosity-average polymerization degree of the component that dissolves in tetrahydrofuran of the crosslinked vinyl chloride-based resin (B) was controlled. Further, the reason that gripping performance during weaving was able to be imparted is because the portion of the component that dissolves in tetrahydrofuran of the crosslinked vinyl chloride-based resin (B) which has a high viscosity-average polymerization degree was set to a suitable blending amount and the shapes of the projections in three directions were controlled. Finally, the reason that spinnability is favorable is because the blending amount of the crosslinked vinyl chloride-based resin (B) was made suitable and the sizes of the projections in three directions were controlled.

EXAMPLES

Below, examples and comparative examples shall be shown and specific embodiments of the present invention explained in greater detail, but the present invention is not limited only to these examples.

The materials used in the examples and comparative examples are as shown below.

(Polyvinyl Chloride-Based Resin (A))

A-1: Homopolymerized product of vinyl chloride, viscosity-average polymerization degree: 500 (TH-500 manufactured by TAIYO VINYL CORPORATION).

A-2: Homopolymerized product of vinyl chloride, viscosity-average polymerization degree: 1,100 (TH-1000 manufactured by TAIYO VINYL CORPORATION).

A-3: Homopolymerized product of vinyl chloride, viscosity-average polymerization degree: 1,350 (TH-1400 manufactured by TAIYO VINYL CORPORATION).

A-4: Homopolymerized product of vinyl chloride, viscosity-average polymerization degree: 2,000 (TH-2800 manufactured by TAIYO VINYL CORPORATION).

200 mg of the resin was dissolved in 50 mL of nitrobenzene, the polymer solution was placed in a 30° C. thermostatic oven, the specific viscosity was measured with an Ubbelohde-type viscometer and the viscosity-average polymerization degree was calculated according to JIS-K6721.

(Crosslinked Vinyl Chloride-Based Resin (B))

B-1: Partially-crosslinked vinyl chloride resin, viscosity-average polymerization degree of the THF-soluble component: 1,600 (GR-1300 T manufactured by Shin-Etsu Chemical Co., Ltd.)

B-2: Partially-crosslinked vinyl chloride resin, viscosity-average polymerization degree of the THF-soluble component: 2,020 (GR-2500S manufactured by Shin-Etsu Chemical Co., Ltd.)

B-3: Partially-crosslinked vinyl chloride resin, viscosity-average polymerization degree of the THF-soluble component: 2,280 (K25S manufactured by KANEKA CORPORATION)

The viscosity-average polymerization degree of the tetrahydrofuran (THF)-soluble component was measured as follows. 1 g of the resin was added to 60 mL of tetrahydrofuran and let stand for about 24 hours. The resin was then sufficiently dissolved using an ultrasonic cleaning machine. The non-soluble components in the THF solution were separated using an ultracentrifugal separator (30,000 rpm×1 hour) and the supernatent THF solvent was extracted. Then, the THF solvent was volatilized and the viscosity-average polymerization degree was measured with a method similar to that for the polyvinyl chloride-based resin (A).

Example 1

A polyvinyl chloride-based resin composition wherein 90 parts by mass of polyvinyl chloride-based resin (A-1) (TH-500 manufactured by TAIYO VINYL CORPORATION), 10 parts by mass of crosslinked vinyl chloride-based resin (B-2) (GR-2500S manufactured by Shin-Etsu Chemical Co., Ltd.), 0.5 parts by mass of an antistatic agent (NEW ELEGAN ASK manufactured by NOF CORPORATION), 3 parts by mass of a hydrotalcite-based complex thermal stabilizer (CP-410A manufactured by Nissan Chemical Corporation), 0.5 parts by mass of an epoxidized soy bean oil (O-130P manufactured by Asahi Denka Co., Ltd.), and 0.8 parts by mass of a ester-based lubricant (EW-100 manufactured by RIKEN VITAMIN CO., LTD.) were blended was mixed in a ribbon blender, melt kneaded using a 40 mm diameter extruder with a cylinder temperature in the range 130-170° C., and pellets were fabricated.

The pellets were melt spun with a 30 mm diameter extruder having apertures with projections in three directions and using a nozzle in which the number of apertures is 120, with a cylinder temperature of 140-190° C., a nozzle temperature in the range of 180±15° C., and an extrusion amount of 10 kg/hour.

Then, the yarn was heat treated for about 0.5-1.5 seconds with a heating cylinder (with conditions for good spinnability in a 200-300° C. atmosphere) provided directly below the nozzle, making a 150 decitex fiber. Next, through a sequence of a step for stretching the melt-spun fiber 300% in a 100° C. air atmosphere and then a step for heat shrinking the stretched fiber in a 120° C. atmosphere until the entire length of the fiber is 75% of that before treatment, a 67 decitex fiber for artificial hair was obtained.

When the cross-sectional shape of the obtained fiber for artificial hair was measured with the abovementioned measurement method using a VHX-500 digital microscope manufactured by Keyence Corporation, the length $L_1$ of the first projection, the length $L_2$ of the second projection, and the length $L_3$ of the third projection were, respectively, $L_1$: 78 μm, $L_2$: 70 μm ($0.9 \times L_1$), and $L_3$: 70 μm ($0.9 \times L_1$) and the ratios of the center C-side widths and the projection end-side widths were $W_{1(0.15)}/W_{1(0.9)}$: 37 μm/23 μm=1.6, $W_{2(0.15)}/W_{2(0.9)}$: 34 μm/16 μm=2.1, and $W_{3(0.15)}/W_{3(0.9)}$: 35 μm/16 μm=2.2.

Examples 2-19 and Comparative Examples 1-10

Other than changing the blends of the polyvinyl chloride-based resin compositions and the cross-sectional shapes of the fibers obtained by melt spinning as shown in Tables 1-3, the fibers for artificial hair in Examples 2-19 and Comparative Examples 1-10 were obtained similarly to that of Example 1.

Examples 20 and 21

Other than the length $L_1$ of the first projection, the length $L_2$ of the second projection, and the length $L_3$ of the third projection all being set to 78 μm or 75 μm, the fibers for artificial hair in Examples 20 and 21 were obtained in similarly to that of Example 1.

[Evaluation]

The spinnability, low glossiness, and grip during weaving of the fibers for artificial hair of the examples and comparative examples were evaluated according to the following evaluation methods and standards. The results are shown in Tables 1-4.

(1) Spinnability

During melt spinning and when the unstretched yarn was made, the occurrence of yarn breakage was observed visually and the following 5-rank evaluation performed.
1: 10-15 breaks/hour
2: 7-9 breaks/hour
3: 4-6 breaks/hour
4: 2 or 3 breaks/hour
5: No greater than 1 break/hour (2) Low Glossiness Bundles of the fibers were observed and the following 5-rank evaluation performed. When determining low glossiness, the vinyl chloride-based fiber M-TYPE manufactured by Denka Company Limited was set as Rank 1 (extreme gloss).
1: Extreme gloss.
2: Gloss.
3: Some gloss.
4: Low gloss.
5: Extremely low gloss.

(3) Grip 3 sets of 30 cm×0.5 g fiber bundles wherein gear working was performed on the fibers for artificial hair of the examples and the comparative examples were fabricated and the upper 2 cm of each was fixed and after being braided such that the length after braiding was in the range of 20-25 cm, the following 5-rank evaluation was performed. When doing so, the vinyl chloride-based fiber M-TYPE manufactured by Denka Company Limited was set as Rank 1 (extremely slippery).
1: Extremely slippery.
2: Slippery.
3: Somewhat slippery.
4: Not slippery.
5: Not at all slippery.

TABLE 1

| | | | | Content Units: Parts by Mass | | | | | |
|---|---|---|---|---|---|---|---|---|---|
| | | | Resin Type | Viscosity-Average Polymerization Degree | Example 1 | Example 2 | Example 3 | Example 4 | Example 5 |
| Resin Composition | Polyvinyl Chloride-based Resin A | | A-1 | 500 | 90 | 95 | 99 | | |
| | | | A-2 | 1100 | | | | 90 | 95 |
| | | | A-3 | 1350 | | | | | |
| | | | A-4 | 2000 | | | | | |
| | Crosslinked Vinyl Chloride-based Resin B | | B-1 | 1600 (THF-soluble component) | | | | | |
| | | | B-2 | 2020 (THF-soluble component) | 10 | 5 | 1 | 10 | 5 |
| | | | B-3 | 2280 (THF-soluble component) | | | | | |
| | Difference between the viscosity-average polymerization degree of A and the viscosity-average polymerization degree of the THF-soluble component of B | | | | 1520 | 1520 | 1520 | 920 | 920 |
| | Additive | | | Antistatic Agent (parts by mass) | 0.5 | 0.5 | 0.5 | 0.5 | 0.5 |
| Fiber for artificial hair | Cross-section | | | Shape | Y-shaped | Y-shaped | Y-shaped | Y-shaped | Y-shaped |
| | | | | Length $L_1$ (μm) | 78 | 75 | 70 | 75 | 81 |
| | | | | Length $L_2$ | $0.9L_1$ | $0.9L_1$ | $0.9L_1$ | $0.9L_1$ | $0.9L_1$ |
| | | | | Length $L_3$ | $0.9L_1$ | $0.9L_1$ | $0.9L_1$ | $0.9L_1$ | $0.9L_1$ |
| | | | | $W_{1(0.15)}/W_{1(0.9)}$ | 1.6 | 1.6 | 1.6 | 1.6 | 1.6 |
| | | | | $W_{2(0.15)}/W_{2(0.9)}$ | 2.1 | 2.1 | 2.1 | 2.1 | 2.1 |
| | | | | $W_{3(0.15)}/W_{3(0.9)}$ | 2.2 | 2.2 | 2.2 | 2.2 | 2.2 |

TABLE 1-continued

Content Units: Parts by Mass

| | | | | | | | | | |
|---|---|---|---|---|---|---|---|---|---|
| | Evaluation | | | Spinnability | | 3 | 4 | 4 | 3 | 4 |
| | | | | Low Glossiness | | 4 | 4 | 3 | 4 | 4 |
| | | | | Grip | | 4 | 4 | 3 | 4 | 4 |

| | | | Resin Type | Viscosity-Average Polymerization Degree | Example 6 | Example 7 | Example 8 | Example 9 | Example 10 |
|---|---|---|---|---|---|---|---|---|---|
| Resin Composition | Polyvinyl Chloride-based Resin A | | A-1 | 500 | | | | | 90 |
| | | | A-2 | 1100 | 99 | | | | |
| | | | A-3 | 1350 | | 90 | 95 | 99 | |
| | | | A-4 | 2000 | | | | | |
| | Crosslinked Vinyl Chloride-based Resin B | | B-1 | 1600 (THF-soluble component) | | | | | |
| | | | B-2 | 2020 (THF-soluble component) | 1 | 10 | 5 | 1 | |
| | | | B-3 | 2280 (THF-soluble component) | | | | | 10 |
| | Difference between the viscosity-average polymerization degree of A and the viscosity-average polymerization degree of the THF-soluble component of B | | | | 920 | 670 | 670 | 670 | 1780 |
| | Additive | | | Antistatic Agent (parts by mass) | 0.5 | 0.5 | 0.5 | 0.5 | 0.5 |
| Fiber for artificial hair | Cross-section | | | Shape | Y-shaped | Y-shaped | Y-shaped | Y-shaped | Y-shaped |
| | | | | Length $L_1$ (μm) | 74 | 70 | 72 | 65 | 65 |
| | | | | Length $L_2$ | $0.9L_1$ | $0.9L_1$ | $0.9L_1$ | $0.9L_1$ | $0.9L_1$ |
| | | | | Length $L_3$ | $0.9L_1$ | $0.9L_1$ | $0.9L_1$ | $0.9L_1$ | $0.9L_1$ |
| | | | | $W_{1(0.15)}/W_{1(0.9)}$ | 1.6 | 1.6 | 1.6 | 1.6 | 1.6 |
| | | | | $W_{2(0.15)}/W_{2(0.9)}$ | 2.1 | 2.1 | 2.1 | 2.1 | 2.1 |
| | | | | $W_{3(0.15)}/W_{3(0.9)}$ | 2.2 | 2.2 | 2.2 | 2.2 | 2.2 |
| | Evaluation | | | Spinnability | 4 | 3 | 4 | 4 | 3 |
| | | | | Low Glossiness | 3 | 4 | 3 | 3 | 4 |
| | | | | Grip | 3 | 4 | 4 | 3 | 4 |

TABLE 2

Content Units: Parts by Mass

| | | | Resin Type | Viscosity-Average Polymerization Degree | Example 11 | Example 12 | Example 13 | Example 14 | Example 15 |
|---|---|---|---|---|---|---|---|---|---|
| Resin Composition | Polyvinyl Chloride-based Resin A | | A-1 | 500 | 95 | 99 | 95 | 95 | 95 |
| | | | A-2 | 1100 | | | | | |
| | | | A-3 | 1350 | | | | | |
| | | | A-4 | 2000 | | | | | |
| | Crosslinked Vinyl Chloride-based Resin B | | B-1 | 1600 (THF-soluble component) | | | | | |
| | | | B-2 | 2020 (THF-soluble component) | | | | 5 | 5 | 5 |
| | | | B-3 | 2280 (THF-soluble component) | 5 | 1 | | | |
| | Difference between the viscosity-average polymerization degree of A and the viscosity-average polymerization degree of the THF-soluble component of B | | | | 1780 | 1780 | 1520 | 1520 | 1520 |
| | Additive | | | Antistatic Agent (parts by mass) | 0.5 | 0.5 | 0.5 | 0.5 | 0.5 |
| Fiber for artificial hair | Cross-section | | | Shape | Y-shaped | Y-shaped | Y-shaped | Y-shaped | Y-shaped |
| | | | | Length $L_1$ (μm) | 72 | 70 | 75 | 59 | 80 |
| | | | | Length $L_2$ | $0.9L_1$ | $0.9L_1$ | $0.9L_1$ | $0.9L_1$ | $0.9L_1$ |
| | | | | Length $L_3$ | $0.9L_1$ | $0.9L_1$ | $0.9L_1$ | $0.9L_1$ | $0.9L_1$ |
| | | | | $W_{1(0.15)}/W_{1(0.9)}$ | 1.6 | 1.6 | 1.6 | 1.6 | 1.2 |
| | | | | $W_{2(0.15)}/W_{2(0.9)}$ | 2.1 | 2.1 | 2.2 | 2.2 | 2.0 |
| | | | | $W_{3(0.15)}/W_{3(0.9)}$ | 2.2 | 2.2 | 1.9 | 2.4 | 2.1 |
| | Evaluation | | | Spinnability | 3 | 3 | 3 | 3 | 4 |
| | | | | Low Glossiness | 4 | 3 | 4 | 4 | 4 |
| | | | | Grip | 4 | 3 | 4 | 5 | 3 |

| | | | Resin Type | Viscosity-Average Polymerization Degree | Example 16 | Example 17 | Example 18 | Example 19 |
|---|---|---|---|---|---|---|---|---|
| Resin Composition | Polyvinyl Chloride-based Resin A | | A-1 | 500 | 95 | 95 | 95 | 95 |
| | | | A-2 | 1100 | | | | |
| | | | A-3 | 1350 | | | | |
| | | | A-4 | 2000 | | | | |
| | Crosslinked Vinyl Chloride-based Resin B | | B-1 | 1600 (THF-soluble component) | | | | |
| | | | B-2 | 2020 (THF-soluble component) | 5 | 5 | 5 | 5 |

TABLE 2-continued

Content Units: Parts by Mass

|  |  |  |  |  |  |  |  |
|---|---|---|---|---|---|---|---|
|  |  | B-3 | 2280 (THF-soluble component) |  |  |  |  |
|  | Difference between the viscosity-average polymerization degree of A and the viscosity-average polymerization degree of the THF-soluble component of B |  |  | 1520 | 1520 | 1520 | 1520 |
|  | Additive | Antistatic Agent (parts by mass) |  | 0.5 | 0.5 | 0.5 | 0.5 |
| Fiber for artificial hair | Cross-section | Shape |  | Y-shaped | Y-shaped | Y-shaped | Y-shaped |
|  |  | Length $L_1$ (μm) |  | 72 | 75 | 70 | 68 |
|  |  | Length $L_2$ |  | $0.9L_1$ | $0.95L_1$ | $0.82L_1$ | $0.95L_1$ |
|  |  | Length $L_3$ |  | $0.82L_1$ | $0.94L_1$ | $0.8L_1$ | $0.8L_1$ |
|  |  | $W_{1(0.15)}/W_{1(0.9)}$ |  | 1.6 | 1.6 | 1.6 | 1.6 |
|  |  | $W_{2(0.15)}/W_{2(0.9)}$ |  | 2.1 | 2.1 | 2.1 | 2.1 |
|  |  | $W_{3(0.15)}/W_{3(0.9)}$ |  | 2.2 | 2.2 | 2.2 | 2.2 |
|  | Evaluation | Spinnability |  | 4 | 5 | 3 | 4 |
|  |  | Low Glossiness |  | 4 | 4 | 4 | 4 |
|  |  | Grip |  | 3 | 5 | 3 | 3 |

TABLE 3

Content Units: Parts by Mass

|  |  | Resin Type | Viscosity-Average Polymerization Degree | Comparative Example 1 | Comparative Example 2 | Comparative Example 3 | Comparative Example 4 | Comparative Example 5 |
|---|---|---|---|---|---|---|---|---|
| Resin Composition | Polyvinyl Chloride-based Resin A | A-1 | 500 | 99.5 | 85 | 95 |  | 95 |
|  |  | A-2 | 1100 |  |  |  |  |  |
|  |  | A-3 | 1350 |  |  |  |  |  |
|  |  | A-4 | 2000 |  |  |  | 95 |  |
|  | Crosslinked Vinyl Chloride-based Resin B | B-1 | 1600 (THF-soluble component) |  |  | 5 |  |  |
|  |  | B-2 | 2020 (THF-soluble component) | 0.5 | 15 |  | 5 | 5 |
|  |  | B-3 | 2280 (THF-soluble component) |  |  |  |  |  |
|  | Difference between the viscosity-average polymerization degree of A and the viscosity-average polymerization degree of the THF-soluble component of B |  |  | 1520 | 1520 | 1100 | 20 | 1520 |
|  | Additive | Antistatic Agent (parts by mass) |  | 0.5 | 0.5 | 0.5 | 0.5 | 0.5 |
| Fiber for artificial hair | Cross-section | Shape |  | Y-shaped | Y-shaped | Y-shaped | Y-shaped | Y-shaped |
|  |  | Length $L_1$ (μm) |  | 68 | 69 | 71 | 77 | 69 |
|  |  | Length $L_2$ |  | $0.9L_1$ | $0.9L_1$ | $0.9L_1$ | $0.9L_1$ | $0.5L_1$ |
|  |  | Length $L_3$ |  | $0.9L_1$ | $0.9L_1$ | $0.9L_1$ | $0.9L_1$ | $0.9L_1$ |
|  |  | $W_{1(0.15)}/W_{1(0.9)}$ |  | 1.6 | 1.6 | 1.6 | 1.6 | 1.6 |
|  |  | $W_{2(0.15)}/W_{2(0.9)}$ |  | 2.1 | 2.1 | 2.1 | 2.1 | 2.1 |
|  |  | $W_{3(0.15)}/W_{3(0.9)}$ |  | 2.2 | 2.2 | 2.2 | 2.2 | 2.2 |
|  | Evaluation | Spinnability |  | 4 | 2 | 4 | 3 | 2 |
|  |  | Low Glossiness |  | 1 | 5 | 2 | 2 | 4 |
|  |  | Grip |  | 2 | 5 | 2 | 4 | 2 |

|  |  | Resin Type | Viscosity-Average Polymerization Degree | Comparative Example 6 | Comparative Example 7 | Comparative Example 8 | Comparative Example 9 | Comparative Example 10 |
|---|---|---|---|---|---|---|---|---|
| Resin Composition | Polyvinyl Chloride-based Resin A | A-1 | 500 | 95 | 95 | 95 | 95 | 95 |
|  |  | A-2 | 1100 |  |  |  |  |  |
|  |  | A-3 | 1350 |  |  |  |  |  |
|  |  | A-4 | 2000 |  |  |  |  |  |
|  | Crosslinked Vinyl Chloride-based Resin B | B-1 | 1600 (THF-soluble component) |  |  |  |  |  |
|  |  | B-2 | 2020 (THF-soluble component) | 5 | 5 | 5 | 5 | 5 |
|  |  | B-3 | 2280 (THF-soluble component) |  |  |  |  |  |
|  | Difference between the viscosity-average polymerization degree of A and the viscosity-average polymerization degree of the THF-soluble component of B |  |  | 1520 | 1520 | 1520 | 1520 | 1520 |
|  | Additive | Antistatic Agent (parts by mass) |  | 0.5 | 0.5 | 0.5 | 0.5 | 0.5 |
| Fiber for artificial hair | Cross-section | Shape |  | Y-shaped | Y-shaped | Y-shaped | Y-shaped | Round |
|  |  | Length $L_1$ (μm) |  | 75 | 74 | 69 | 80 | 80 (radius) |
|  |  | Length $L_2$ |  | $0.9L_1$ | $0.9L_1$ | $0.9L_1$ | $0.9L_1$ | $0.9L_1$ |
|  |  | Length $L_3$ |  | $0.9L_1$ | $0.9L_1$ | $0.9L_1$ | $0.9L_1$ | $0.9L_1$ |
|  |  | $W_{1(0.15)}/W_{1(0.9)}$ |  | 1.0 | 3.0 | 1.6 | 1.6 | — |
|  |  | $W_{2(0.15)}/W_{2(0.9)}$ |  | 2.1 | 2.1 | 1.4 | 3.1 | — |
|  |  | $W_{3(0.15)}/W_{3(0.9)}$ |  | 2.2 | 2.2 | 1.5 | 3.0 | — |

TABLE 3-continued

Content Units: Parts by Mass

| | Evaluation | | | |
|---|---|---|---|---|
| Spinnability | 4 | 1 | 5 | 1 | 4 |
| Low Glossiness | 4 | 4 | 4 | 4 | 5 |
| Grip | 2 | 5 | 2 | 5 | 1 |

TABLE 4

Content Units: Parts by Mass

| | | Resin Type | Viscosity-Average Polymerization Degree | Example 21 | Example 22 |
|---|---|---|---|---|---|
| Resin Composition | Polyvinyl Chloride-based Resin A | A-1 | 500 | 90 | 90 |
| | | A-2 | 1100 | | |
| | | A-3 | 1350 | | |
| | | A-4 | 2000 | | |
| | Crosslinked Vinyl Chloride-based Resin B | B-1 | 1600 (THF-soluble component) | | |
| | | B-2 | 2020 (THF-soluble component) | 10 | 10 |
| | | B-3 | 2280 (THF-soluble component) | | |
| | Difference between the viscosity-average polymerization degree of A and the viscosity-average polymerization degree of the THF-soluble component of B | | | 1520 | 1520 |
| | Additive | | Antistatic Agent (parts by mass) | 0.5 | 0.5 |
| Fiber for artificial hair | Cross-section | | Shape | Y-shaped | Y-shaped |
| | | | Length $L_1$ (μm) | 78 | 75 |
| | | | Length $L_2$ | L1 | L1 |
| | | | Length $L_3$ | L1 | L1$_1$ |
| | | | $W_{1(0.15)}/W_{1(0.9)}$ | 1.6 | 1.6 |
| | | | $W_{2(0.15)}/W_{2(0.9)}$ | 2.1 | 2.1 |
| | | | $W_{3(0.15)}/W_{3(0.9)}$ | 2.2 | 2.2 |
| Evaluation | | | Spinnability | 3 | 3 |
| | | | Low Glossiness | 4 | 4 |
| | | | Grip | 3 | 3 |

In Comparative Example 1, polyvinyl chloride-based resin (A) is greater than 99 parts by mass and crosslinked vinyl chloride-based resin (B) is less than 1 part by mass, so the rough shape of the surface of the yarn became small and the low glossiness and grip decreased greatly.

In Comparative Example 2, polyvinyl chloride-based resin (A) is less than 90 parts by mass and crosslinked vinyl chloride-based resin (B) is greater than 10 parts by mass, so the incompatible component became large and spinnability decreased greatly.

Comparative Example 3 is a case of the viscosity-average polymerization degree of the component that dissolves in tetrahydrofuran of the crosslinked vinyl chloride-based resin (B) being less than 1,800 and the roughness of the yarn surface shrank, so low glossiness and grip worsened.

In Comparative Example 4, the difference in viscosity-average polymerization degree between the polyvinyl chloride-based resin (A) and the component that dissolves in tetrahydrofuran of the crosslinked vinyl chloride-based resin (B) is 20 and because the difference is lower than 600, low glossiness decreased.

In Comparative Example 5, the length $L_2$ of the second projection is shorter than $0.8L_1$, so spinnability and grip worsened.

In Comparative Example 6, the ratio of the cross-sectional center-side and the projection end-side widths of the first projection $W_{1(0.15)}/W_{1(0.9)}$ is smaller than 1.2, so grip decreased.

In Comparative Example 7, the ratio of the cross-sectional center-side and the projection end-side widths of the first projection $W_{1(0.15)}/W_{1(0.9)}$ is greater than 2.5, so spinnability worsened remarkably.

In Comparative Example 8, both the ratio $W_{2(0.15)}/W_{2(0.9)}$ of the cross-sectional center-side and projection end-side widths of the second projection and the ratio $W_{3(0.15)}/W_{3(0.9)}$ of the cross-sectional center-side and projection end-side widths of the third projection are smaller than 1.8, so friction between yarns decreased and grip worsened.

In Comparative Example 9, both the ratios $W_{2(0.15)}/W_{2(0.9)}$ and $W_{3(0.15)}/W_{3(0.9)}$ are greater than 2.5, so the polyvinyl chloride-based resin composition did not stably exit the nozzle apertures during spinning and spinnability worsened.

In Comparative Example 10, due to the round shape, gripping performance worsened.

INDUSTRIAL APPLICABILITY

A fiber for artificial hair having a specific viscosity-average polymerization degree of a polyvinyl chloride-based resin and a viscosity-average polymerization degree of a component that dissolves in tetrahydrofuran of a crosslinked vinyl chloride-based resin, a specific difference in the viscosity-average polymerization degrees, and a specific shape has low glossiness and can impart grip. Further, the fiber of the present invention can be manufactured by being stably melt spun and therefore is industrially advantageous.

REFERENCE SIGNS LIST

1 First projection
2 Second projection
3 Third projection
10 Fiber for artificial hair
C Center of cross-sectional shape

The invention claimed is:

1. A fiber for artificial hair using a polyvinyl chloride-based resin composition, wherein
the polyvinyl chloride-based resin composition comprises 90-99 parts by mass of a polyvinyl chloride-based resin (A) having a viscosity-average polymerization degree of 450-1,450 and 1-10 parts by mass of a crosslinked vinyl chloride-based resin (B) having a viscosity-average polymerization degree for a component that is soluble in tetrahydrofuran of 1,900-2,300,
the difference between the viscosity-average polymerization degree of the polyvinyl chloride-based resin (A) and the viscosity-average polymerization degree for the component that is soluble in tetrahydrofuran of the crosslinked vinyl chloride-based resin (B) is 600-1,850, and,
the cross-sectional shape of the fiber for artificial hair has a first projection, a second projection, and a third projection extending outward from a center C of the cross-sectional shape and when the length of the first projection from the center C is set as $L_1$, wherein $L_1$ is 65-80 μm, the length of the second projection from the center C is set as $L_2$, and the length of the third projection from the center C is set as $L_3$, the shapes of the projections satisfy (2) and (3) below:
(2) the ratio of a width $W_{1(0.15)}$ of the first projection at a distance of $0.15L_1$ from the center C and a width $W_{1(0.9)}$ of the first projection at a distance of $0.9L_1$ from the center C ($W_{1(0.15)}/W_{1(0.9)}$) is 1.5-2.3;
(3) the ratio of a width $W_{2(0.15)}$ of the second projection at a distance of $0.15L_2$ from the center C and a width $W_{2(0.9)}$ of the second projection at a distance of $0.9L_2$ from the center C ($W_{2(0.15)}/W_{2(0.9)}$) is 2.0-2.2; and the ratio of a width $W_{3(0.15)}$ of the third projection at a distance of $0.15L_3$ from the center C and a width $W_{3(0.9)}$ of the third projection at a distance of $0.9L_3$ from the center C ($W_{3(0.15)}/W_{3(0.9)}$) is 1.9-2.4,
and wherein the length $L_1$ of the first projection, length $L_2$ of the second projection, and the length $L_3$ of the third projection from the center C satisfy $L_3 \leq L_2$, $0.8L_1 \leq L_2 \leq 0.95L_1$ and $0.8L_1 \leq L_3 \leq 0.95L_1$.

2. The fiber for artificial hair according to claim 1, containing 0.1-5.0 parts by mass of at least one thermal stabilizer selected from the group consisting of tin-based thermal stabilizers, Ca—Zn-based thermal stabilizers, hydrotalcite-based thermal stabilizers, epoxy-based thermal stabilizers, and β-diketone-based thermal stabilizers with respect to a total of 100 parts by mass of the polyvinyl chloride-based resin (A) and the crosslinked vinyl chloride-based resin (B).

3. The fiber for artificial hair according to claim 2, containing 0.1-5.0 parts by mass of at least one thermal stabilizer selected from the group consisting of tin-based thermal stabilizers, Ca-Zn-based thermal stabilizers, hydrotalcite-based thermal stabilizers, epoxy-based thermal stabilizers, and β-diketone-based thermal stabilizers with respect to a total of 100 parts by mass of the polyvinyl chloride-based resin (A) and the crosslinked vinyl chloride-based resin (B).

4. The fiber for artificial hair according to claim 1, containing 0.1-5.0 parts by mass of at least one thermal stabilizer selected from the group consisting of tin-based thermal stabilizers, Ca—Zn-based thermal stabilizers, hydrotalcite-based thermal stabilizers, epoxy-based thermal stabilizers, and β-diketone-based thermal stabilizers with respect to a total of 100 parts by mass of the polyvinyl chloride-based resin (A) and the crosslinked vinyl chloride-based resin (B).

* * * * *